(12) United States Patent
Ben-Jonathan et al.

(10) Patent No.: US 11,834,423 B2
(45) Date of Patent: Dec. 5, 2023

(54) SMALL MOLECULE PROLACTIN RECEPTOR INHIBITORS, PHARMACEUTICAL COMPOSITIONS AND TREATMENT METHODS USING SUCH INHIBITORS

(71) Applicants: University of Cincinnati, Cincinnati, OH (US); The Hebrew University of Jerusalem, Jerusalem (IL); University of Texas System, Austin, TX (US)

(72) Inventors: Nira Ben-Jonathan, Cincinnati, OH (US); Eric R. Hugo, Cincinnati, OH (US); Edward J. Merino, Cincinnati, OH (US); Abraham J. Domb, Jerusalem (IL); Armen N. Akopian, Austin, TX (US)

(73) Assignees: University of Cincinnati, Cincinnati, OH (US); University of Texas System, Austin, TX (US); The Hebrew University of Jerusalem, Jerusalem (IL)

( * ) Notice: Subject to any disclaimer, the term of this patent is extended or adjusted under 35 U.S.C. 154(b) by 149 days.

(21) Appl. No.: 17/491,452

(22) Filed: Sep. 30, 2021

(65) Prior Publication Data
US 2022/0024881 A1 Jan. 27, 2022

Related U.S. Application Data

(62) Division of application No. 16/331,728, filed as application No. PCT/US2017/050586 on Sep. 8, 2017, now Pat. No. 11,168,061.

(60) Provisional application No. 62/410,907, filed on Oct. 21, 2016, provisional application No. 62/385,948, filed on Sep. 9, 2016.

(51) Int. Cl.
| | |
|---|---|
| *A61P 35/00* | (2006.01) |
| *C07D 253/075* | (2006.01) |
| *A61K 31/135* | (2006.01) |
| *A61K 31/415* | (2006.01) |
| *A61K 31/475* | (2006.01) |
| *A61K 31/53* | (2006.01) |
| *A61K 45/06* | (2006.01) |
| *A61K 9/00* | (2006.01) |
| *A61K 33/243* | (2019.01) |
| *A61K 31/122* | (2006.01) |
| *A61K 31/337* | (2006.01) |
| *A61K 31/4184* | (2006.01) |
| *A61K 31/437* | (2006.01) |

(52) U.S. Cl.
CPC ........ *C07D 253/075* (2013.01); *A61K 9/0019* (2013.01); *A61K 9/0053* (2013.01); *A61K 31/135* (2013.01); *A61K 31/415* (2013.01); *A61K 31/475* (2013.01); *A61K 31/53* (2013.01); *A61K 45/06* (2013.01); *A61P 35/00* (2018.01); *A61K 31/122* (2013.01); *A61K 31/337* (2013.01); *A61K 31/4184* (2013.01); *A61K 31/437* (2013.01); *A61K 33/243* (2019.01)

(58) Field of Classification Search
CPC ... C07D 253/075; A61P 35/00; A61K 9/0019; A61K 9/0053; A61K 31/135; A61K 31/415; A61K 31/475; A61K 31/53; A61K 45/06
See application file for complete search history.

(56) References Cited

U.S. PATENT DOCUMENTS

| | | |
|---|---|---|
| 2010/0022456 A1 | 1/2010 | Christensen et al. |
| 2010/0152125 A1 | 6/2010 | Agar et al. |
| 2011/0098309 A1 | 4/2011 | Look et al. |
| 2013/0345219 A1 | 12/2013 | Lee et al. |

FOREIGN PATENT DOCUMENTS

WO      2008055972 A2      5/2008

OTHER PUBLICATIONS

Gura, Science Nov. 7, 1997: vol. 278. No. 5340., pp. 1041-1042.
R.N. 515177-27-2 et al: "1,2,4-Triazin-3(2H)-one, 5-amino-6- [(4-chloro-2-hydroxyphenyl)amino methyl" In: "1,2,4-Triazin-3(2H)-one,5-amino-6- [(4-chloro-2-hydroxyphenyl)amino methyl", May 14, 2003 (May 14, 2003), KP55657304.
Leaf, Clifton, Health Administrator vol. XVII, No. 1:171-183, 2005.
Pubchem CID 6156011, Sep. 15, 2005, pp. 1-12.
"Expert Scientific Group on Phase one Clinical Trials Final Report" Nov. 30, 2006, pp. C1, C35-C38.
Cancer Drug Design and Discovery Neidle, Stephen, ed. (Elsevier/Academic Press, 2008) pp. 427-431.
Tao Liu et al, Synthesis and screening of a cyclic peptide library: Discovery of small-molecule ligands against human prolactin receptor; Bioorganic & Medicinal Chemistry, 17:1026-1033, 2009.
Extended European Search Report (EESR) for corresponding European Application No. 17849571.9 dated Jan. 22, 2020.
International Search Report & Written Opinion for corresponding PCT/US2017050586 dated Oct. 27, 2017.
Kamb, Nature Reviews Drug Discovery 4, 161-165 (Feb. 2005).
Kola, Nature Reviews Drug Discovery 3, 711-715 (2004).
Roberts, Jr. et al. JAMA292 (17): 2130-2140 (2004).

*Primary Examiner* — Jared Barsky
(74) *Attorney, Agent, or Firm* — Dinsmore & Shohl LLP (57) ABSTRACT

Small molecule inhibitors (SMIs) of the Prolactin receptor, pharmaceutical compositions of the SMIs, and methods for treating patients suffering from disorders characterized increased expression or excitation of the Prolactin receptor, including breast cancer, prostate cancer and nociceptive pain disorders such as migraine headache, by administering pharmaceutical compositions of SMIs are provided.

5 Claims, 4 Drawing Sheets

Fig. 4

SMALL MOLECULE PROLACTIN RECEPTOR INHIBITORS, PHARMACEUTICAL COMPOSITIONS AND TREATMENT METHODS USING SUCH INHIBITORS

PRIORITY CLAIM

This application is a divisional of U.S. application Ser. No. 16/331,728, filed Mar. 8, 2019, which is a § 371 National Stage Entry of International Application No. PCT/US2017/050586, filed Sep. 8, 2017, which claims priority to U.S. Provisional Application Ser. No. 62/385,948, filed Sep. 9, 2016, and U.S. Provisional Application Ser. No. 62/410,907, filed Oct. 21, 2016, the entire disclosures of which are incorporated herein by this reference.

TECHNICAL FIELD

Embodiments of the invention relate to small molecule inhibitors of the prolactin receptor and pharmaceutical compositions and methods of use effective for the treatment of patients suffering from breast cancer, nociceptive pain, and migraine headache.

BACKGROUND

Each year, over a million women worldwide are diagnosed with breast cancer, accounting for 25% of all female cancers. About 1 in 8 women are predicted to develop this disease during her lifetime. Over the last two decades, single and combination chemotherapy, based on results from clinical trials, has led to a considerable reduction in morbidity and increased survival of breast cancer patients. However, more recently, progress has seemingly been stalled.

An effort to identify biomarkers that would predict the response to a particular therapy ensued and this approach has been well validated with respect to several tumor-related biomarkers. Examples include expression of estrogen receptors (ER) in a large percentage of breast tumors and prevention stimulation of ER-positive tumors by estrogens by either blocking the ER by drugs such as tamoxifen and raloxifene which are members of the growing class of Selective Estrogen Receptor Modulators (SERMs), or by preventing conversion of steroid precursors to estrogen by drug such as anastrazole and letrozole, which belong to the family of aromatase inhibitor. Genetic profiling has also been successful in identifying breast cancer patients with amplification of the HER-2 gene, whose tumors can carry as many as 50 to 100 copies instead of the usual 2 copies per cell. HER-2 positive patients respond well to the humanized monoclonal antibody trastuzumab. Personalized medicine has also been applied to patients with TOP2A aberrations, who respond better to anthracyclines than those with normal TOP2A gene. In addition, variants of the genes BRCA1 and BRCA2, found in a small percentage of the population, can identify susceptible individuals in families with a history of breast cancer. The next step/phase in the advancement of breast cancer therapy was the search for new molecular targets followed by the design of appropriate modalities directed against these targets. One of the more promising of these new targets that has yet to be fully exploited is the Prolactin Receptor (PRLR).

Prolactin (PRL) is a 25 kDa hormone produced by the anterior pituitary whose main target is the breast, where it stimulates lobulo-alveolar growth, differentiation and pro-survival. PRL is a pleiotropic hormone whose biological effects extend to the support of lactation, control of steroidogenesis, maternal behavior, osmoregulation, and effects on metabolism and the immune system. In humans, PRL is also produced in many extrapituitary sites, including the breast, where it acts as an autocrine/paracrine factor. PRL belongs to a family of proteins, the lactogens, which share structural homology and some overlapping functions. The three most prominent members are hPRL, growth hormone (hGH) and placental lactogen (hPL) which diverged from a common ancestral gene. They share a tertiary structure made of four anti-parallel, up-up, downdown helical bundle, but have a limited primary sequence homology except for an identical location of the disulfide bridges. Despite their structural differences, each of the lactogens is capable of binding to the human PRLR and triggering its signaling cascade. PRL is associated with a higher risk of developing breast cancer and enhancement of tumor growth and metastasis, as revealed by epidemiological studies that higher serum PRL levels in premenopausal women are associated with increased risk of breast cancer. This association is strengthened by many in vitro studies showing that PRL stimulates breast cancer cell (BCC) proliferation and survival. Furthermore, an ectopic production of PRL by BCC stimulates their proliferation in an autocrine manner.

The fact that PRL reaches the breast not only from the pituitary via the blood but also from local sources has often been often overlooked. Using RT-PCR, metabolic labeling and a sensitive bioassay, the present investigators reported a 10-15 fold higher PRL production in breast adipose tissue than the adjacent epithelium (Zinger et al. *J. Clin. Endocrinol. Metab.*, 2003, 88, 689-96, incorporated fully herein). Other studies have shown that the majority of breast carcinomas stained positive for PRL.

Previous studies by the present investigators also established that PRL is overexpressed in MDA-MB-435 BCC enhanced tumor growth and upregulated Bcl-2 (Liby, K. et al. *Breast Cancer Res. Treat.*, 2003, 79, 241-52, incorporated fully herein); and further studies confirmed that pretreatment of BCC with low doses of PRL antagonizes cytotoxicity by taxol, vinblastine, doxorubicin and cisplatin, albeit at different efficacies (Lapensee, E. W. et al. *Carcinogenesis*, 2009, 30, 1298-304, incorporated fully herein).

An emerging concept in the development of chemoresistance is the contribution made by hormones. Unlike the major focus of research on estrogens as mitogens in breast cancer, only few studies have examined their role in chemoresistance. This oversight is enigmatic because stimulation of tumor growth by estrogens involves not only increased cell proliferation but also reduced cell death. A potential joint contribution by PRL and estrogens towards chemoresistance has not previously been extensively investigated.

The PRLR is a member of the class I cytokine receptor superfamily which are non-tyrosine kinase, single-pass membrane receptors. The gene encoding the PRLR is located on chromosome 5, and is comprised of 10 exons spanning 100 kb. The receptor has a tripartite organization, comprised of an extracellular ligand binding domain (LBD) which confers specificity, a short transmembrane domain, and an intracellular domain (ICD) which initiates signaling upon receptor occupancy. Alternative splicing generates at least nine variants of the human PRLR, which primarily differ in the lengths and composition of their cytoplasmic domains, and ultimately different signalling properties (Swaminathan, G. et al. *J. Mammary Gland Biol. Neoplasia*, 2008, 13, 81-91, incorporated fully herein). In addition to its cognate receptor, hGH also binds to the PRLR, and so does hPL, which does not have a distinct receptor of its own.

Thus, increasing evidence suggests that the PRLR is an excellent target in the treatment of breast cancer. There are several reasons why the PRLR itself should be a prime target of molecular inhibition. First, the three lactogens, which are dissimilar in critical interacting residues, do not induce identical conformational changes in the receptor. Instead, each imposes a different stability on the active complex, thus affecting its dynamics and the binding parameters of the associated partners. Hence, there are multiple outputs from the same receptor, all of which may have relevance to cancer biology. The best way to block this multifaceted output is to target the cascade at the most upstream event, binding to the PRLR. Second, inhibiting PRL signaling at receptor level would prevent any cross talk interactions with other pro-cancer pathways. Finally, simply targeting PRL production/release would be ineffective, due to the potential of activation of the signaling pathway by the other lactogens.

Underscoring the need to develop specific inhibitors of PRL signaling is the fact that treatment of breast cancer patients with the dopamine agonist bromocriptine, which blocks pituitary PRL release, does not have positive effects on tumor progression. Therefore, the development of molecules that can selectively block the PRL signaling pathway has been undertaken by several laboratories. Several PRLR antagonists, made by point mutations in the PRL molecule via a combination of deletion and mutations, or by fusions, have been developed. Approaches have included development of a modified S179D hPRL intended to mimic phosphorylated PRL and act as an inhibitor, and development of G129R hPRL designed to disrupt receptor dimerization; both of which failed to meet expected therapeutic potential due to various nonspecific interactions/interferences. Several mutated PRL molecules have shown a reasonable antagonistic activity in vitro and in experimental animals; however the engineered PRL approach is not efficacious for treating patients because of the necessity to deliver proteins by injections, their short half-life, and the difficulty in achieving appropriate and sustained therapeutic levels. Several antibody-based approaches for targeting the PRLR were developed but are hampered by finding a suitable antibody specific for the human version of the PRLR and the need to 'humanize' such antibodies to avoid immunological rejection.

High PRLR expression is also known to be positively correlated with resistance to chemotherapy and increased invasiveness prostate tumors. Multiple studies have shown that activation of the PRLR receptor promotes prostate tumor growth and similarly to breast cancer, overexpression of PRL significantly increases tumor size and expression of survival proteins in xenograft models.

More recently, significant, localized increases in PRL concentration have been implicated in the onset of migraine headaches, and with nociceptive pain induction generally. A nociceptor is a type of receptor at the end of the axon of a sensory neuron that responds to damaging or potentially damaging stimuli by sending danger signals to the spinal cord and brain in a process generally referred to as nociception. Nociceptive pain results from stimulation of the nociceptor and the source of the stimuli may be the external or internal environment (thermal, pressure/mechanical, traumatic, chemical, e.g.). Subsequent studies suggest that neutralization of PRLR signaling in animal models by specific antibodies or by mutated PRL antagonists reduced the pain response. Such treatments for humans, however, suffer from the same drawbacks as with cancer, and for pain management, the balance against the overall health of the patient leans away from the use of potentially problematic treatment regimens.

In light of the limitations of a protein based strategy together with ineffectiveness of extant treatments for breast cancer and prostate cancer, and the potential for application to control of nociceptive pain response, there is an ongoing critical need to develop novel therapies targeted at the PRLR, and of particular benefit would be small molecule inhibitors which can be given orally.

SUMMARY

Accordingly, embodiments of the present invention provide novel small molecule inhibitors of PRLR formulated as pharmaceutical compositions and administered as both injectable solutions and oral dosing forms for the treatment of breast cancer, prostate cancer and for control of nociceptive pain.

One embodiment is directed to a pharmaceutical composition comprising: a small molecule PRLR inhibitor according to Formula I or Formula II; and, optionally, at least one pharmaceutically acceptable carrier, and, optionally, at least one pharmaceutically acceptable salt, wherein Formula I is structurally depicted as:

and
Formula II is structurally depicted as:

and further wherein, $R_1$, and $R_2$ are independently selected from $-CY_3$, linear or cyclic alkyl, halogen, cycloalkyl, heterocycloalkyl, alkenyl, alkynyl, aryl, heteroaryl, and H; and X is selected from $-NH_2$, halogen, $-OH$, $-SH$, $-NO_2$, $-COOH$, $-SO_3H$, and $-SO_2NH_2$, a, b, and c are independently 0, 1, 2, or 3, n is 0 or an integer between 1 and 10; and each Y is independently H or halogen selected from Cl, Br, F, and I.

Another embodiment provides methods for treating a patient suffering from a disorder characterized by increased expression of Prolactin receptor (PRLR). The methods comprise administering one or more pharmaceutical compositions comprising at least one small molecule PRLR inhibitor according to Formula I or Formula II as set forth above; and, optionally, at least one pharmaceutically acceptable carrier, and, optionally, at least one pharmaceutically acceptable salt. According to specific embodiments the disorder comprises cancer or a disorder characterized by a nociceptive pain response.

Yet another embodiment is directed to methods for reducing or substantially eliminating acquired resistance to chemotherapeutic drugs in a patient undergoing or about to undergo treatment for cancer comprising a regimen of one or more chemotherapeutic drugs. Methods comprise administering to the patient a pharmaceutical composition comprising at least one small molecule PRLR inhibitor according to Formula I or Formula II as set forth above; and, optionally, at least one pharmaceutically acceptable carrier, and, optionally, at least one pharmaceutically acceptable salt, wherein administering is initiated before, during, or subsequent to chemotherapy.

These and other embodiments and aspects will be further clarified and expounded upon by reference to the Detailed Description and Figures below. Figures are provided to illustrate specific embodiments and advantages and should not be construed as limiting the scope of the invention as defined by the appended claims.

DETAILED DESCRIPTION OF THE INVENTION

Embodiments of the invention provide small molecule inhibitors of PRLR signaling, pharmaceutical compositions comprising one or more of the small molecule inhibitor compounds, and methods for treating cancer, methods for reducing resistance to chemotherapy, and methods for treating patients suffering from conditions characterized by nociceptive pain by administering one or more of the small molecule inhibitor compounds. Based on previous in silico molecular docking work, the present investigators identified two structural formulae possessing enhanced binding and inhibition potential vis a vis the PRLR. Specific, exemplary embodiments of compounds of Formula I as defined herein include SMI-6 and derivatives of SMI-6, and specific embodiments of compounds of Formula II as defined herein include SMI-1 and derivatives of SMI-1. Both specific exemplary compounds strongly interact with the ligand binding domain of human PRLR (hPRLR) at binding affinities (Kd) of 1.2 and 3.3 for SMI-1 and SMI-6, respectively, and both were confirmed pharmacologically to block PRLR signaling in multiple cellular assays.

One embodiment is directed to a pharmaceutical composition comprising: a small molecule PRLR inhibitor according to Formula I or Formula II; and, optionally, at least one pharmaceutically acceptable carrier, and, optionally, at least one pharmaceutically acceptable salt, wherein Formula I is structurally depicted as:

and
Formula II is structurally depicted as:

and further wherein, $R_1$, and $R_2$ are independently selected from —$CY_3$, linear or cyclic alkyl, halogen, cycloalkyl, heterocycloalkyl, alkenyl, alkynyl, aryl, heteroaryl, and H; and X is selected from —$NH_2$, halogen, —OH, —SH, —$NO_2$, —COOH, —$SO_3H$, and —$SO_2NH_2$; a, b, and c are independently 0, 1, 2, or 3, n is 0 or an integer between 1 and 10; and each Y is independently H or halogen selected from Cl, Br, F, and I. According to specific embodiments, $R_1$ is selected from —$CY_3$, halogen and H, $R_2$ is selected from $CY_3$, halogen, linear C2-C3 alkyl, a, b and c are independently 0, 1 or 2, and each Y is independently F or H; and for Formula II, $R_1$ is para and selected from —$CY_3$, halogen and H, and n is 0, 1 or 2.

As utilized herein, "halogen" or "halogen atom" means fluorine, chlorine, bromine, or iodine. The term "alkyl" refers to a substituted or unsubstituted saturated, straight-chain or branched hydrocarbon group that contains from 1 to 20 carbon atoms, preferably from 1 to 10 carbon atoms, for example a n-octyl group, especially from 1 to 6 carbon atoms, i.e. 1, 2, 3, 4, 5, or 6. Specific examples of alkyl groups include methyl, ethyl, propyl, iso-propyl, n-butyl, iso-butyl, sec-butyl, tert-butyl, n-pentyl, iso-pentyl, n-hexyl and 2,2-dimethylbutyl. Specific examples of suitable substitutions include —NH$_2$, halogen, —OH, —SH, —NO$_2$, —COOH, —SO$_3$H, and —SO$_2$NH$_2$. Very specific examples are selected from Cl, F, and —OH. Exemplary, non-limiting preferred substituted alkyl included mono-, di- and tri-halogenated methyl and ethyl wherein the halogen is selected from Fluorine and Chlorine.

The term "alkenyl" refers to an at least partially unsaturated straight-chain or branched hydrocarbon group that contains from 2 to 20 carbon atoms, preferably from 2 to 10 carbon atoms, especially from 2 to 6, i.e. 2, 3, 4, 5 or 6, carbon atoms. Specific examples of alkenyl groups include ethenyl (vinyl), propenyl (allyl), iso-propenyl, butenyl, ethinyl, propinyl, butinyl, acetylenyl, propargyl, iso-prenyl and hex-2-enyl group. Preferably, alkenyl groups have one or two double bonds.

The term "alkynyl" refers to an at least partially unsaturated substituted or unsubstituted, straight-chain or branched hydrocarbon group that contains from 2 to 20 carbon atoms, preferably from 2 to 10 carbon atoms, especially from 2 to 6 carbon atoms, i.e. 2, 3, 4, 5 or 6. Specific examples of alkynyl groups are ethynyl, propynyl, butynyl, acetylenyl and propargyl groups. More specifically, alkynyl groups have one or two triple bonds, and even more specifically alkynyl groups have one triple bond.

The term "cycloalkyl" refers to a saturated or partially unsaturated (for example, a cycloalkenyl group) substituted or unsubstituted cyclic group that contains one (or more, in the case of polycyclic) rings (preferably 1 or 2), and contains from 3 to 14 ring carbon atoms, preferably from 3 to 10 (especially 3, 4, 5, 6 or 7) ring carbon atoms. Specific examples of cycloalkyl groups are cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, adamantane (i.e. tricycle[3.3.1.1$^{3,7}$]decane), cyclopentylcyclohexyl and cyclohex-2-enyl. Specific examples of suitable substitutions include —NH$_2$, halogen, —OH, —SH, —NO$_2$, —COOH, —SO$_3$H, and —SO$_2$NH$_2$. Very specific examples are selected from Cl, F, and —OH.

The term "heterocycloalkyl" refers to a substituted or unsubstituted cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). A heterocycloalkyl group has preferably 1 or 2 rings containing from 3 to 10 (especially 3, 4, 5, 6 or 7) ring atoms (preferably selected from C, O, N and S). Specific examples include piperidyl, prolinyl, imidazolidinyl, piperazinyl, morpholinyl, urotropinyl, pyrrolidinyl, tetra-hydrothiophenyl, tetrahydropyranyl, tetrahydrofuryl and 2-pyrazolinyl group and also lactames, lactones, cyclic imides and cyclic anhydrides. Specific examples of suitable substitutions include —NH$_2$, halogen, —OH, —SH, —NO$_2$, —COOH, —SO$_3$H, and —SO$_2$NH$_2$. Very specific examples are selected from Cl, F, and —OH.

The term "aryl" refers to a substituted or unsubstituted aromatic group that contains one (or more, in the case of polycyclic aryl) rings containing from 6 to 14 ring carbon atoms, preferably from 6 to 10 (especially 6) ring carbon atoms. Examples are phenyl, naphthyl and biphenyl groups. Specific examples of suitable substitutions include —NH$_2$, halogen, —OH, —SH, —NO$_2$, —COOH, —SO$_3$H, and —SO$_2$NH$_2$. Very specific examples are selected from Cl, F, and —OH.

The term "heteroaryl" refers to a substituted or unsubstituted aromatic group that contains one (or more, in the case of polycyclic heteroaryl) rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably O, S or N). Examples are pyridyl (for example, 4-pyridyl), imidazolyl (for example, 2-imidazolyl), phenylpyrrolyl (for example, 3-phenylpyrrolyl), thiazolyl, iso-thiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (for example, 3-pyrazolyl) and iso-quinolinyl groups. Specific examples of suitable substitutions include —NH$_2$, halogen, —OH, —SH, —NO$_2$, —COOH, —SO$_3$H, and —SO$_2$NH$_2$. Very specific examples are selected from Cl, F, and —OH.

Small molecule inhibitors may be present in a pharmaceutical composition as a pharmaceutically acceptable salt. By pharmaceutically acceptable salt it is meant those salts, within the scope of medical science, which are suitable for use in contact with the tissues of humans and lower animals without undue toxicity, irritation, allergic response and the like, and are commensurate with a reasonable benefit/risk ratio. Pharmaceutically acceptable salts are well known in the art. For example, suitable pharmaceutically acceptable salts of compounds according to the present invention may be prepared by mixing the compounds of the invention with a pharmaceutically acceptable acid (including inorganic and organic acids). Suitable pharmaceutically acceptable salts of the compounds of the present invention therefore include acid addition salts. Suitable pharmaceutically acceptable organic acids for making this salts include, but are not limited to the following: acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, malonic acid, mandelic acid, methanesulfonic acid, mucic acid, nitric acid, pamoic acid, pantothenic acid, phosphoric acid, oxalic acid, succinic acid, sulfuric acid, tartaric acid acid, p-toluenesulfonic acid, and the like. Inorganic acid addition salts are hydrochloric, hydrobromic, phosphoric, and sulfuric acid salts.

The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

Embodiments of the invention contemplate that the small molecule inhibitors may be formulated into a pharmaceutical composition comprising a pharmaceutically acceptable carrier. Preferably the SMI is provided in pharmaceutical grade purity.

The term "pharmaceutically acceptable carrier" is intended to include solvents, dispersion media, coatings, antibacterial and anti-fungal agents, isotonic and absorption delaying agents, and the like. The use of such media and agents for pharmaceutically active substances is well known in the art. Except in so far as any conventional media or agent is incompatible with the compound, use thereof in the therapeutic compositions and methods of treatment is contemplated. Supplementary active compounds may also be incorporated into the compositions according to embodiments of the present invention. It is especially advantageous to formulate parenteral compositions in dosage unit form for ease of administration and uniformity of dosage.

The term "dosage unit form" as used herein refers to physically discrete units suited as unitary dosages for the individual to be treated; each unit containing a predetermined quantity of compound(s) calculated to produce the desired therapeutic effect in association with the required pharmaceutical earner. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

Sterile injectable solutions can be prepared by incorporating the SMI compound in the required amount in an appropriate solvent with one or a combination of the ingredients discussed herein, as required, followed by filtered sterilisation. Generally, dispersions are prepared by incorporating the SMI compound into a sterile vehicle which contains a basic dispersion medium and the required other ingredients. Tablets, troches, pills, capsules and the like may also comprise the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it may further comprise a liquid carrier. Various other materials can be present as coatings or to otherwise modify the physical form of the dosage unit. For instance, tablets, pills, or capsules can be coated with shellac, sugar or both. A syrup or elixir may comprise the SMI inhibitor, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the SMI compound may be incorporated into sustained/extended-release, controlled release, delayed release preparations and formulations.

In very specific embodiments, the pharmaceutical composition comprises a small molecule PRLR inhibitor compound according to Formula I:

In other very specific embodiments, the pharmaceutical composition comprises a small molecule PRLR inhibitor compound according to Formula II:

According to some embodiments, the pharmaceutical composition may be formulated as an injectable solution or as an oral dosing form. SMI compound may be included in the pharmaceutical composition in any therapeutically relevant amount, which may vary based on specifics of the patient, such as size, gender, health status and the like. Specific compositions are formulated with a molar concentration of SMI compound up to 10 µM, up to 5 µM, between 1 µM and 10 µM, between 5 µM and 10 µM or between 1 µM and 5 µM. As will be apparent to an ordinary clinician, amounts may be adjusted higher if lesser amounts are well-tolerated by the patient. Concentrations of total SMI compound up to 25 µM, including continuously all values in-between, are contemplated.

Other embodiments of the invention are directed to methods of treating patients suffering from a disorder characterized by increased expression of Prolactin receptor (PRLR). According to specific embodiments, the disorder is cancer. According to more specific embodiments, the disorder comprises breast or prostate cancer. Method generally comprises administering a pharmaceutical composition comprising one or more SMI compounds according to the invention. According to very specific embodiments, The SMI compound comprises SMI-1 or SMI-6.

Convenient modes of administration of SMI compounds of the invention include parenteral (for example, subcutaneous, intravenous, intramuscular, intradermal, intraperitoneal, intrathecal, intraocular, intranasal, intraventricular injection or infusion techniques), oral, pulmonary (e.g. inhalation), transdermal application, topical (e.g. creams or gels or powders), or rectal administration. Depending on the route of administration, the formulation and/or compound may be coated with a material to protect the compound from the action of enzymes, acids and other natural conditions which may inactivate the therapeutic activity of the compound. In other formulations the dosage form may be coated for extended, controlled, or delayed release by methods well-known in the art.

Dispersions of the SMI compounds according to the invention may also be prepared in glycerol, liquid polyethylene glycols, oils, and mixtures thereof. Under ordinary conditions of storage and use, pharmaceutical preparations may contain a preservative to prevent the growth of microorganisms. Pharmaceutical compositions suitable for injection include: sterile aqueous solutions (where water soluble), or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

SMI compounds of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the SMI compound(s) may be incorporated with excipients and used in the form of ingestible tablets, buccal tablets, troches, capsules, elixirs, suspensions, syrups, wafers, and the like. Suitable dosages may be obtained by single or multiple administrations.

According to some embodiments of the invention, the pharmaceutical composition is administered in conjunction with one or more chemotherapeutic agents that affect cellular microtubules. Chemotherapeutic agents may be selected from cisplatin, demecolcine, nocodazole, vinblastine, paclitaxel (taxol), and combinations thereof.

Other embodiments of the invention are directed to methods for reducing or substantially eliminating acquired resistance to chemotherapeutic drugs in a patient undergoing or about to undergo treatment for cancer comprising a regimen of one or more chemotherapeutic drugs by administering one or more of the SMI compounds according to embodiments of the invention. According to specific embodiments, the cancer comprises breast or prostate cancer. Depending on whether the treatment is intended for prophylactic purposes or as a response to observation of resistance, the SMI compounds may be administered before, during, and/or after initiation of a regimen of one or more chemotherapeutic drugs. Non-limiting examples of chemotherapeutic drugs with a problematic resistance profile but which are effectively addressed by methods disclosed herein include cisplatin, demecolcine, nocodazole, vinblastine, and paclitaxel (taxol), and generally any chemotherapeutic agent that acts on microtubules.

The nociceptive pain response may also be controlled via inhibition of PRLR. Nociceptive pain is that which results from triggering/stimulating/activating a pain-receptor and may be considered a sensory nerve response; whereas non-nociceptive pain does not implicate pain receptors. A specific example of a condition characterized by nociceptive pain comprise migraine headache. Although the term "migraine headache" encompasses various types of headaches, all implicate stimulation of pain receptors. Embodiments of the invention provide methods of treating a patient suffering from a condition characterized by nociceptive pain by administering one or more of the SMI compounds according to Formula I or II as defined herein, and more specifically by administering SMI-1 or SMI-6. According to specific embodiments, administering comprises a peripheral parenteral or oral route and the small molecule inhibitor is formulated as an injectable solution or an oral dosing form at a concentration of between 1 µM and 5 µM. In other specific embodiments administering comprises a central route and the small molecule inhibitor is formulated as an injectable solution at a concentration of between 1 µM and 25 µM. Although endpoints are provided, the scope of the embodiment includes all values between the endpoints. As will be readily understood by a clinician of ordinary skill in the art, doses may be divided as necessary depending on the health and tolerance level of an individual patient.

The following Examples are set forth to illustrate specific embodiments and should not be construed as narrowing the scope of the invention as defined by the appended claims.

EXAMPLES

Example 1. Blockade of PRL-Induced Invasion of Breast Cancer Cells is Confirmed

Figure 1A:
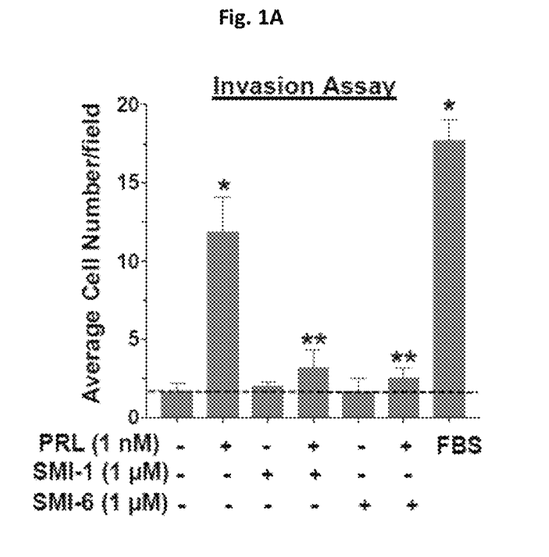
FIG. 1A. Bar graph showing inhibition of PRL-induced invasion of breast cancer cells by SMI-1 and SMI-6.
Figure 1B:
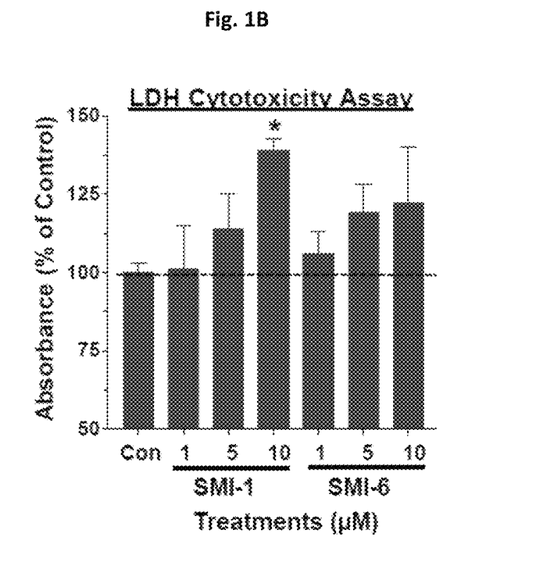
FIG. 1B. Bar graph showing only minimal cytotoxicity at indicated concentrations.

Both SMI-1 and SMI-6 at 1 µM concentrations abrogated PRL-induced invasion of MDA-MB-468 breast cancer cells, using Boyden chambers (FIG. 1A). The LDH cytotoxicity assay revealed that the SMIs had minimal toxicity, especially at 10-fold higher doses (FIG. 1B).

Example 2. Blockade of Autocrine PRL-Induced Cell Proliferation is Demonstrated

Figure 2:
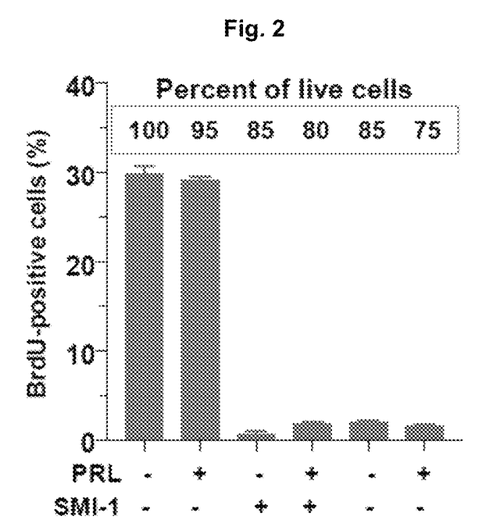
FIG. 2. Bar graph showing suppression of autocrine PRL-dependent BrdU uptake in Jurkat lymphocytes by 1 M of each SMI, as determined by flow cytometry; the top panel indicates percent of live cells.

To examine whether the SMIs can suppress cell proliferation that is driven by autocrine PRL, Jurkat human lymphocytes were utilized, which produce large amounts of autocrine PRL. Autocrine PRL in lymphocytes is well known to promote cell proliferation. The cells were incubated for 24 hrs in 2% charcoal-stripped serum (which is devoid on exogenous lactogenic hormones) with 1 µM of SMI-1 or SMI-6, and then with 1 nM PRL for 24 hrs. BrdU uptake was analyzed by flow cytometry. As shown in FIG. 2, added PRL had no effect, likely because of receptor saturation by autocrine PRL. Notably, both SMI-6 and SMI-1 completely blocked cell proliferation, while reducing cell viability by only 10-20%.

Figure 3:
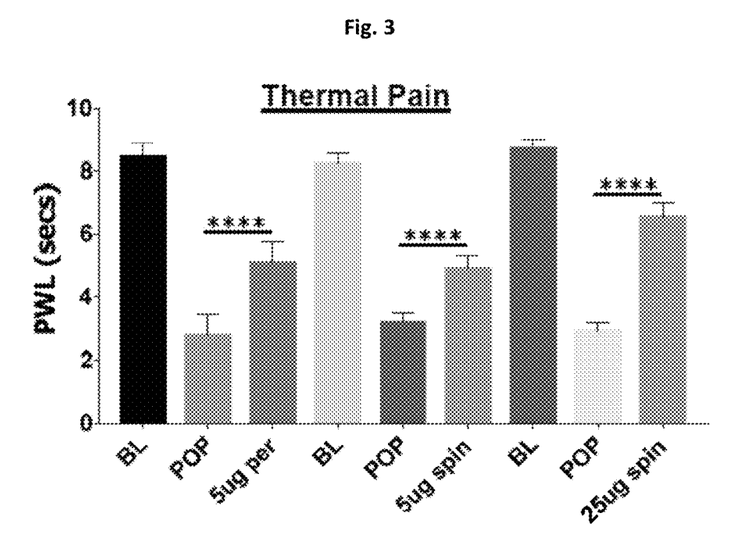
FIG. 3. Bar graph demonstrating the effects of SMI-6 on thermal nociception; female mice were operated on the right hind paw; one day post-surgery, heat hyperalgesia was applied and paw withdrawal latency (PWL) was measured; BL—baseline: POP—postoperative pain; SMI-6 was applied either peripherally (5 g per), or spinally 5 g spin or 25 g spin SMI-6; each value is a mean±SME of 6 mice/treatment.

Example 3. Abrogation of Peripheral Pain by Exemplary Compound SMI-6 is Demonstrated Female mice were operated on the right hind paw. One day after surgery, 5 µg SMI-6 was applied either peripherally or centrally/spinally (5 µg or 25 µg) and mice were subjected to thermal nociception or mechanical allodynia (increased sensitization to tactile stimuli). As evident in FIG. 3, SMI-6 showed a dose-dependent alleviation of thermal pain, which was applied to the inured paw by means of a short radiant heat beam and measurement of leg withdrawal latency. SMI-6 at the 25 µg dose was effective in alleviating thermal pain by as much as 75%.

Figure 4:
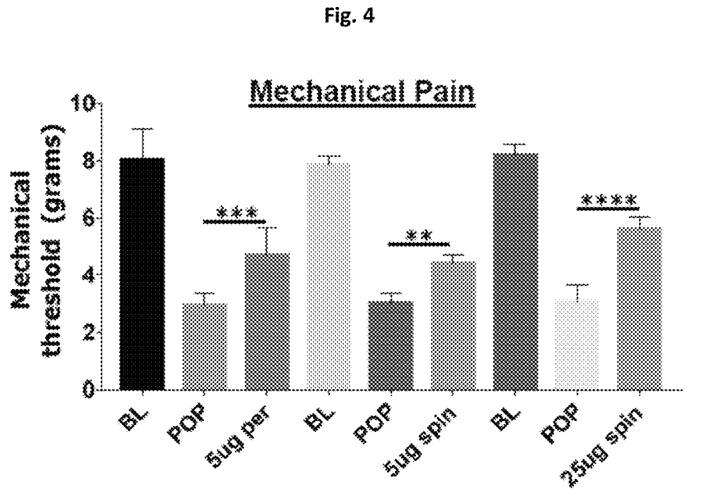
FIG. 4. Bar graph demonstrating effects of SMI-6 on mechanical allodynia; female mice were operated on the right hind paw; one day postsurgery, an anesthesiometer was used to measure leg withdrawal threshold against increasing mechanical pressure on the animal right hind paw. BL—baseline: POP—postoperative pain; SMI-6 was applied either peripherally (5 g per), or spinally (5 g or 25 g); each value is a mean±SME of 6 mice/treatment.

For evaluating allodynia, an anesthesiometer was used, which applied a constant ramp of increasing mechanical pressure to the injured paw. Withdrawal latency was measured in grams. FIG. 4 shows that SMI-6 was equally as effective in abrogating mechanical pain.

The invention claimed is:

1. A pharmaceutical composition comprising:
   a small molecule prolactin receptor (PRLR) inhibitor according to Formula II or a pharmaceutical salt thereof; and
   at least one pharmaceutically acceptable carrier,
   wherein Formula II is structurally depicted as:

and wherein:
   $R_1$ is selected from —$CY_3$, linear or cyclic alkyl, halogen, cycloalkyl, heterocycloalkyl, alkenyl, alkynyl, aryl, heteroaryl, and H;
   X is selected from —$NH_2$, halogen, —OH, —SH, —$NO_2$, —COOH, —$SO_3H$, and —$SO_2NH_2$;
   n is 0 or an integer between 1 and 10; and
   each Y is independently H or halogen selected from Cl, Br, F, and I.

2. The pharmaceutical composition according to claim 1, wherein $R_1$ is para and selected from —$CY_3$, halogen and H, and n is 0, 1 or 2.

3. The pharmaceutical composition according to claim 1, wherein the small molecule PRLR inhibitor is a compound according to Formula II and structurally depicted as:

4. The pharmaceutical composition according to claim 1, formulated as an injectable solution or as an oral dosing form.

5. The pharmaceutical composition according to claim 4, wherein the molar concentration of inhibitor is up to 10 μM, up to 5 μM, between 1 μM and 10 μM, between 5 μM and 10 μM or between 1 μM and 5 μM.

\* \* \* \* \*